United States Patent [19]
Seed et al.

[11] Patent Number: 5,858,752
[45] Date of Patent: Jan. 12, 1999

[54] FUCOSYLTRANSFERASE GENES AND USES THEREOF

[75] Inventors: Brian Seed, Boston, Mass.; Jan Holgersson, Stockholm, Sweden

[73] Assignee: The General Hospital Corporation, Boston, Mass.

[21] Appl. No.: 483,151

[22] Filed: Jun. 7, 1995

[51] Int. Cl.⁶ .............................. C12N 9/10; C07K 1/00; C12P 21/06; C07H 21/04
[52] U.S. Cl. ..................... 435/193; 530/350; 435/69.1; 435/252.3; 435/320.1; 536/23.2; 536/23.5; 536/23.53
[58] Field of Search ........................... 435/252.3, 6, 69.1, 435/7.6, 12, 193, 320.1; 536/23.2, 23.5, 23.52

[56] References Cited

FOREIGN PATENT DOCUMENTS

WO 94/23021  10/1994  WIPO.

OTHER PUBLICATIONS

Bevilacqua et al., Science 243:1160 (1989).
Hsu–Lin et al., J. Biol. Chem. 259:9121 (1984).
Stenberg et al., J. Cell Biol. 101:880 (1985).
Johnston et al., Blood 69: 1401 (1987).
Geng et al., Nature 343:757 (1990).
McEver et al., J. Clin. Invest. 84:92 (1989).
Bonfanti et al., Blood 73: 1109 (1989).
Larsen et al., Cell 59:305 (1989).
Hamburger et al., Blood 75:550 (1990).
Lowe et al., Cell 63:475 (1990).
Sako et al., Cell 75:1179 (1993).
Kukowska–Latallo et al., Genes Dev. 4:1288 (1990).
Goelz et al., Cell 63:1349 (1990).
Lowe et al., J. Biol. Chem. 266:17467 (1991).
Weston et al., J. Biol. Chem. 267:4152 (1992).
Weston et al., J. Biol. Chem. 267:24575 (1992).
Sasaki et al., J. Biol. Chem. 269:14730 (1994).
Natsuka et al., J. Biol. Chem. 269: 16789 (1994).
Holmes et al., J. Biol. Chem. 261:3737 (1986).
Goelz et al., Biol. Chem. 269: 1033 (1994).
Kreider et al., Oncogene 7:135 (1992).
Horst et al., Nucleic Acids Res. 19:4556 (1991).
Aruffo et al., Cell 61:1303–1313 (1990).
Zettlmeissl et al., DNA Cell Biol. 9:347 (1990).
Levinovitz et al., J. Cell Biol. 121:449 (1993).
Fukuda et al., J. Biol. Chem. 259:10925 (1984).
Spooncer et al., J. Biol. Chem. 259:4792 (1984).
Weston et al., Molecular Cloning of a Fourth Member of a Human α(1,3)Fucosyltransferease Gene Family, J. Biol. Chem. 267:24575–24584, 1992.

*Primary Examiner*—Robert A. Wax
*Assistant Examiner*—Tekchand Saidha
*Attorney, Agent, or Firm*—Clark & Elbing LLP

[57] ABSTRACT

Purified DNA encoding α(1,3)fucosyltransferase and the recombinant proteins expressed from such DNA are disclosed. The recombinant fucosyltransferase polypeptides are used to fucosylate proteins to produce therapeutics useful for the treatment of disease, e.g., an adverse immune reaction such as septiciemia or septic shock.

12 Claims, 9 Drawing Sheets

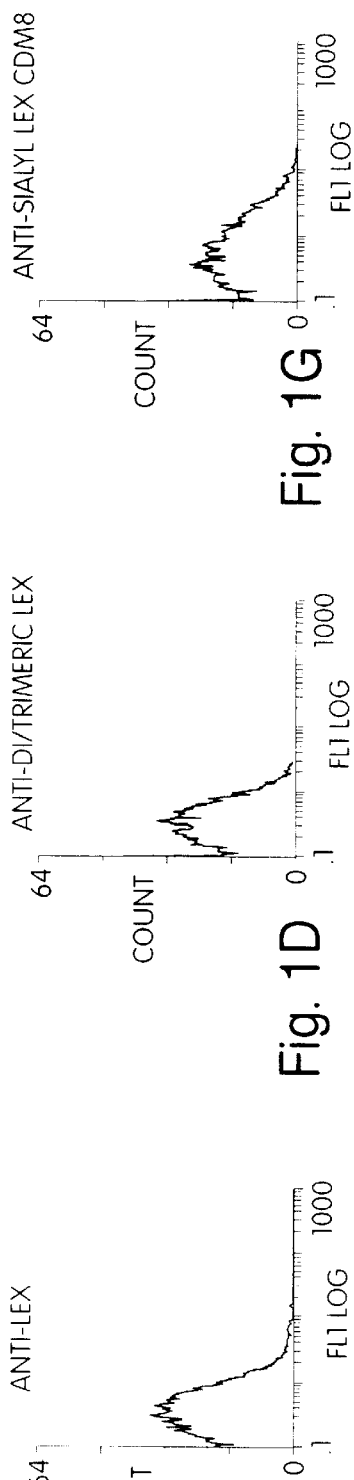

```
   1 gtagccaaggttcctctccatctcaccagagcctgctggaggggaatcaaacaagcctgg
  61 acctgaggctgggactagcttttcctgtttctggagtggatgccaaccccctgcccaccag
 121 cctgcctgtccacgccagggacacacagactccttcccttttccagactggaaagcccccct
 181 cctgggagagcaggaaggaagcaacctgcaactcttccagccctggaccttgggctgaac
 241 ctacagttcaagggtgcctctgttggagaggctgctgtgatttgaaaatcttctttcctt
 301 ggtgacaattccagaaggctccagatgaattgtattgggtaccaccccaccaggaggctg
                                    M  N  C  I  G  Y  H  P  T  R  R  L
 361 cgggcctggggcggcctagctggaggagcaacattcatggtaatttggttttttctggctg
      R  A  W  G  G  L  A  G  G  A  T  F  M  V  I  W  F  F  W  L
 421 tggggatcagctcctggaagtgcccctgtgcctcagtccacactcaccatccttatctgg
      W  G  S  A  P  G  S  A  P  V  P  Q  S  T  L  T  I  L  I  W
 481 cactggccttttcaccaaccggccgccagagctacctggtgacacctgcactcgctatggc
      H  W  P  F  T  N  R  P  P  E  L  P  G  D  T  C  T  R  Y  G
 541 atggccagctgccgtctgagtgctaaccggagcctgctagccagtgctgatgctgtggtc
      M  A  S  C  R  L  S  A  N  R  S  L  L  A  S  A  D  A  V  V
 601 ttccaccaccgtgagctgcaaacccggcaatctctcctacccctggaccagaggccacac
      F  H  H  R  E  L  Q  T  R  Q  S  L  L  P  D  Q  R  P  H
 661 ggacagccttgggtctgggcctccatggaatcgcccagtaatacccatggtctccatcgc
      G  Q  P  W  V  W  A  S  M  E  S  P  S  N  T  H  G  L  H  R
 721 ttccggggcatcttcaactgggtgctgagctatcggcgtgattcagatatctttgtaCcc
      F  R  G  I  F  N  W  V  L  S  Y  R  R  D  S  D  I  F  V  P
 781 tacggtcgcttggagcctctctctgggcccacatccccactaccggccaaaagcaggatg
      Y  G  R  L  E  P  L  S  G  P  T  S  P  L  A  K  S  R  M
 841 gctgcctgggtgatcagcaatttccaggagcggcagcagcgtgcaaagctgtaccggcag
      A  A  W  V  I  S  N  F  Q  E  R  Q  Q  R  A  K  L  Y  R  Q
 901 ctggcccctcatctgcaggtggatgtgttcggtcgcgccagCggacggccccctatgcgct
      L  A  P  H  L  Q  V  D  V  F  G  R  A  S  G  R  P  L  C  A
 961 aattgtctgctgcccactttggcccggtaccgcttctacctggcctttgagaactcacag
      N  C  L  L  P  T  L  A  R  Y  R  F  Y  L  A  F  E  N  S  Q
1021 catcgggactacatcactgagaagttctggcgcaatgccctggcggctggtgctgtaccc
      H  R  D  Y  I  T  E  K  F  W  R  N  A  L  A  A  G  A  V  P
1081 gtggcgctgggacctcctcgggccacctacgaggcttttgtgccaccagatgcctttgta
      V  A  L  G  P  P  R  A  T  Y  E  A  F  V  P  P  D  A  F  V
1141 cacgtggacgacttcagctctgcccgtgaactggctgtcttcctcgtcagcatgaatgag
      H  V  D  D  F  S  S  A  R  E  L  A  V  F  L  V  S  M  N  E
1201 agtcgttatcgtggcttctttgcttggcgagaccggctccgtgtgcggctcctggtgac
      S  R  Y  R  G  F  F  A  W  R  D  R  L  R  V  R  L  L  G  D
1261 tggagggagcgcttctgcaccatctgtgcccgctacccttacttgccccgcagccaggtc
      W  R  E  R  F  C  T  I  C  A  R  Y  P  Y  L  P  R  S  Q  V
1321 tatgaagaccttgaaagctggttccaggcttgaactcctgctgctgggagaggctggatg
      Y  E  D  L  E  S  W  F  Q  A  *
1381 ggtgggagactgatgttgaaaccaaagagctgggcatccaggcttttggtcaccatggca
1441 ctaccccaaggcttttcctgttcagtgagcaggaattcaggatataaggagaaaactggg
1501 ctgagatgcctggtgggctttagagtaggggcccaggataagagacaatgaattaatgag
1561 gagcatatggggaaggtggctgagggtccctgacttaccttgacccatggctgaaggctc
1621 catgccatggctggagctgggaccctacacttctatagtcaaggtgcttagcctcaagg
1681 ttgcagatgcaccctctagtactctgggtgcagactgtacactgggcgcaggggttgtg
1741 gaaggacagtgcagatgattctggcttttgacaccacagttcccccagggaaagaggca
1801 ctactaataaaaac 1814
```

FIG. 3

(SEQ ID NO: 1 & 2)

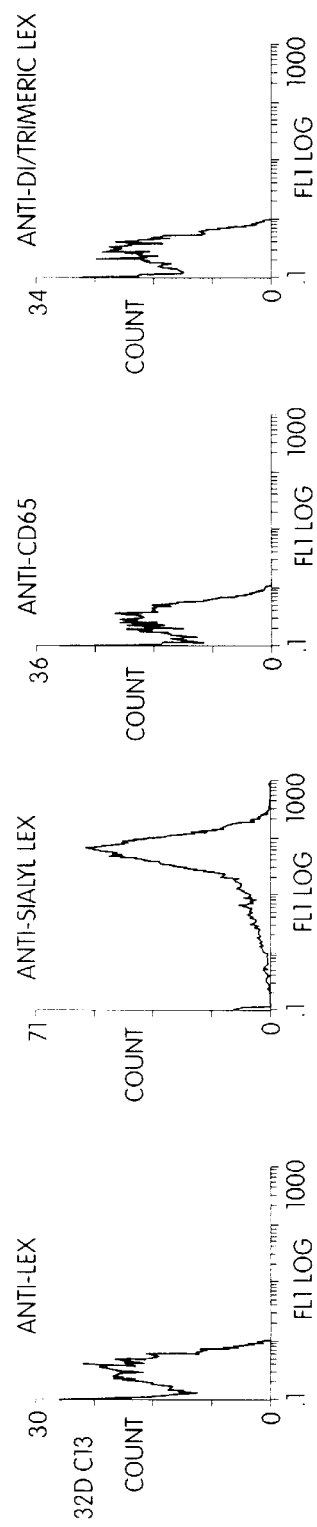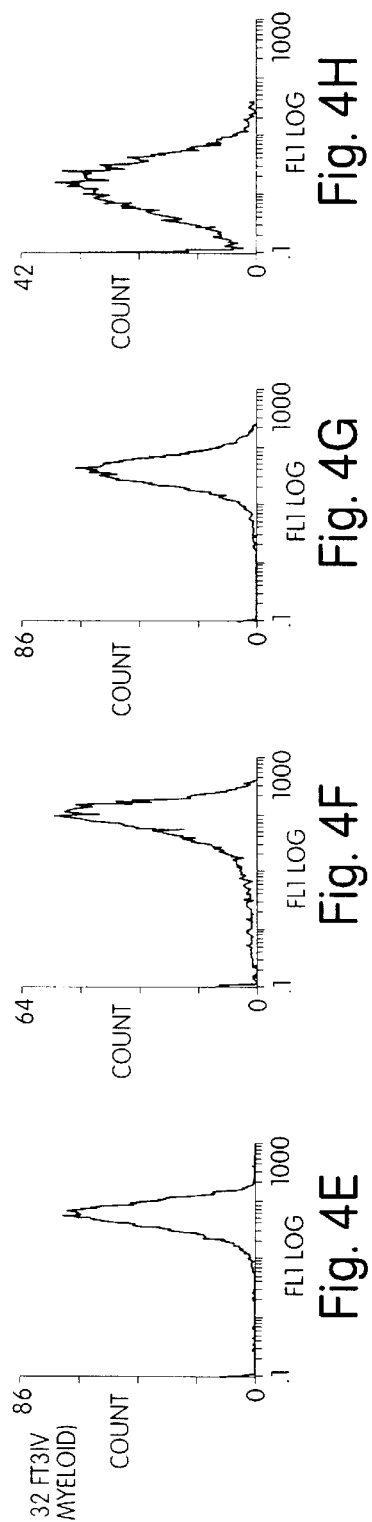

(SEQ ID NO: 3)

```
   1 GGCACGCTGC CTGTTCGCGC CATGGGGGCA CCGTGGGgCT CGCCGACGGC
  51 GGCGGCGGGC GGGCGGCGCG GGTGGCGCCG AGGCCGGGGG CTGCCATGGA
 101 CCGTCTGTGT GCTGGCGGCC GCCGGCTTGA CGTGTACGGC GCTGATCACC
 151 TACGCTTGCT GGGGCAGCT GCCGCCGCTG CCTGGGCGTC GCCAACCCCG
 201 TCGCGACCGG TGGGCGTGCT GCTGTGGTGG GAGCCCTTCG GGGGCGCGAT
 251 CAGCGCCCCG AGGCCGCCCC CTGACTGCCG GCTGCGCTTC AACATCAGCG
 301 GCTGCCGCCT GCTCACCGAC ACGCGCGTCC TACGGAGAGG CTCAGGCCGT
 351 GCTTTTCCAC CACCGCGACC TCGTGAAGGG GCCCCCCGAC TGGCCCCCGC
 401 CCTGGGGCAT CCAGGCGCAC ACTGCCGAGG AGGTGGATCT GCGCGTGTTG
 451 GACTACGAGG AGGCAGCGGC GGCGGCAGAA GCCCTGGCGA CCTCCAGCCC
 501 CAGGCCCCGG GCCAAGCGCT GGGTTTGGAT GAACTTCGAG TCGCCCTCGC
 551 ACTCCCCGGG GCTGCGAAGC TGGCAAGTA ACCTCTTCAA CTGGACGCTC
 601 TCCTACCGGG CGGACTCGGA CGTCTTTGTG CCTTATGGCT ACCTCTACCC
 651 CAGAAGCCAC CCCGGCGACC CGCCCTCAGG CCTGGCCCCG CCACTGTCCA
 701 GGAAACAGGG GCTGGTGGCA TGGGTGGTGA GCCACTGGGA CGAGCGCCAG
 751 GCCCGGGTCC GCTACTACCA CCAACTGAGC CAACATGTGA CCGTGGACGT
 801 GTTCGGCCGG GGCGGGCCGG GGCAGCCGGT GCCCGAAATT GGGCTCCTGC
 851 ACACAGTGGC CCGCTACAAG TTCTACCTGG CTTTCGAGAA CTCGCAGCAC
 901 CTGGATTATA TCACCGAGAA GCTCTGGCGC AACGCGTTGC TCGCTGGGGC
 951 GGTGCCGGTG GTGCTGGGCC CAGACCGTGC CAACTACGAG CGCTTTGTGC
1001 CCGCGGCGC CTTCATCCAC GTGGACGACT TCCCAAGTGC CTCCTCCCTG
1051 GCCTCGTACC TGCTTTTCCT CGACCGCAAC CCCGCGGTCT ATCGCCGCTA
1101 CTTCCACTGG CGCCGGAGCT ACGCTGTCCA CATCACCTCC TTCTGGGACG
1151 AGCCTTGGTG CCGGGTGTGC CAGGCTGTAC AGAGGGCTGG GACCGGCCCA
1201 AGAGCATACG GAACTTGGCC AGCTGGTTCG AGCGGTGAAG CCGCGCTCCC
1251 CTGGAAGCGA CCCAGGGGAG GCCAAGTTGT CAGCTTTTTG ATCCTCTACT
```

Fig. 6A

```
1301 GTGCATCTCC TTGACTGCCC GCATCATGGG AGTAAGTTCT TCAAACACCC
1351 ATTTTTGCTC TATGGGAAAA AAACGATTTA CCAATTAATA TTACTCAGCA
1401 CAGAGATGGG GGCCCGGTTT CCATATTTTT TGCACAGCTA GCAATTGGGC
1451 TCCCTTTGCT GCTGATGGGC ATCATTGTTT AGGGGTGAAG GAGGGGGTTC
1501 TTCCTCACCT TGTAACCAGT GCAGAAATGA AATAGCTTAG CGCAAGAAGC
1551 CGTTGAGGCG GTTTCCTGAA TTTCCCCATC TGCCACAGGC CATATTTGTG
1601 GCCCGTGCAG CTTCCAAATC TCATACACAA CTGTTCCCGA TTCACGTTTT
1651 TCTGGACCAA GGTGAAGCAA ATTTGTGGTT GTAGAAGGAG CCTTGTTGGT
1701 GGAGAGTGGA AGGACTGTGG CTGCAGGTGG GACTTTGTTG TTTGGATTCC
1751 TCACAGCCTT GGCTCCTGAG AAAGGTGAGG AGGGCAGTCC AAGAGGGGCC
1801 GCTGACTTCT TTCACAAGTA CTATCTGTTC CCCTGTCCTG TGAATGGAAG
1851 CAAAGTGCTG GATTGTCCTT GGAGGAAACT TAAGATGAAT ACATGCGTGT
1901 ACCTCACTTT ACATAAGAAA TGTATTCCTG AAAAGCTGCA TTTAAATCAA
1951 GTCCCAAATT CATTGACTTA GGGGAGTTCA GTATTTAATG AAACCCTATG
2001 GAGAATTTAT CCCTTTACAA TGTGAATAGT CATCTCCTAA TTTGTTTCTT
2051 CTGTCTTTAT GTTTTTCTAT AACCTGGATT TTTTAAATCA TATTAAAATT
2101 ACAGATGTGA AAATAAAAAA AAAAAAAAAA AAAA
```

Fig. 6B (SEQ ID NO: 4)

```
  1 MGAPWGSPTA AAGGRRGWRR GRGLPWTVCV LAAAGLTCTA LITYACWGQL
 51 PPLPWASPTP SRPVGVLLWW EPFGGAISAP RPPPDCRLRF NISGCRLLTD
101 RASYGEAQAV LFHHRDLVKG PPDWPPPWGI QAHTAEEVDL RVLDYEEAAA
151 AAEALATSSP RPRAKRWVWM NFESPSHSPG LRSLASNLFN WTLSYRADSD
201 VFVPYGYLYP RSHPGDPPSG LAPPLSRKQG LVAWVVSHWD ERQARVRYYH
251 QLSQHVTVDV FGRGGPGQPV PEIGLLHTVA RYKFYLAFEN SQHLDYITEK
301 LWRNALLAGA VPVVLGPDRA NYERFVPRGA FIHVDDFPSA SSLASYLLFL
351 DRNPAVYRRY FHWRRSYAVH ITSFWDEPWC RVCQAVQRAG DRPKSIRNLA
401 SWFER*
```

Fig. 6C 5,858,752

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1814 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GTAGCCAAGG | TTCCTCTCCA | TCTCACCAGA | GCCTGCTGGA | GGGGAATCAA | ACAAGCCTGG | 60 |
| ACCTGAGGCT | GGGACTAGCT | TTCCTGTTTC | TGGAGTGGAT | GCCAACCCCC | TGCCCACCAG | 120 |
| CCTGCCTGTC | CACGCCAGGG | ACACACAGAC | TCCTTCCCTT | TCCAGACTGG | AAAGCCCCT | 180 |
| CCTGGGAGAG | CAGGAAGGAA | GCAACCTGCA | ACTCTTCCAG | CCCTGGACCT | TGGGCTGAAC | 240 |
| CTACAGTTCA | AGGGTGCCTC | TGTTGGAGAG | GCTGCTGTGA | TTTGAAAATC | TTCTTTCCTT | 300 |
| GGTGACAATT | CCAGAAGGCT | CCAGATGAAT | TGTATTGGGT | ACCACCCAC | CAGGAGGCTG | 360 |
| CGGGCCTGGG | GCGGCCTAGC | TGGAGGAGCA | ACATTCATGG | TAATTTGGTT | TTTCTGGCTG | 420 |
| TGGGGATCAG | CTCCTGGAAG | TGCCCCTGTG | CCTCAGTCCA | CACTCACCAT | CCTTATCTGG | 480 |
| CACTGGCCTT | TCACCAACCG | GCCGCCAGAG | CTACCTGGTG | ACACCTGCAC | TCGCTATGGC | 540 |
| ATGGCCAGCT | GCCGTCTGAG | TGCTAACCGG | AGCCTGCTAG | CCAGTGCTGA | TGCTGTGGTC | 600 |
| TTCCACCACC | GTGAGCTGCA | AACCCGGCAA | TCTCTCCTAC | CCCTGGACCA | GAGGCCACAC | 660 |
| GGACAGCCTT | GGGTCTGGGC | CTCCATGGAA | TCGCCCAGTA | ATACCCATGG | TCTCCATCGC | 720 |
| TTCCGGGGCA | TCTTCAACTG | GGTGCTGAGC | TATCGGCGTG | ATTCAGATAT | CTTTGTACCC | 780 |
| TACGGTCGCT | TGGAGCCTCT | CTCTGGGCCC | ACATCCCCAC | TACCGGCCAA | AAGCAGGATG | 840 |
| GCTGCCTGGG | TGATCAGCAA | TTTCCAGGAG | CGGCAGCAGC | GTGCAAAGCT | GTACCGGCAG | 900 |
| CTGGCCCCTC | ATCTGCAGGT | GGATGTGTTC | GGTCGCGCCA | GCGGACGGCC | CCTATGCGCT | 960 |
| AATTGTCTGC | TGCCCACTTT | GGCCCGGTAC | CGCTTCTACC | TGGCCTTTGA | GAACTCACAG | 1020 |
| CATCGGGACT | ACATCACTGA | GAAGTTCTGG | CGCAATGCCC | TGGCGGCTGG | TGCTGTACCC | 1080 |
| GTGGCGCTGG | GACCTCCTCG | GGCCACCTAC | GAGGCTTTTG | TGCCACCAGA | TGCCTTTGTA | 1140 |
| CACGTGGACG | ACTTCAGCTC | TGCCCGTGAA | CTGGCTGTCT | TCCTCGTCAG | CATGAATGAG | 1200 |
| AGTCGTTATC | GTGGCTTCTT | TGCTTGGCGA | GACCGGCTCC | GTGTGCGGCT | CCTGGGTGAC | 1260 |
| TGGAGGGAGC | GCTTCTGCAC | CATCTGTGCC | CGCTACCCTT | ACTTGCCCCG | CAGCCAGGTC | 1320 |
| TATGAAGACC | TTGAAAGCTG | GTTCCAGGCT | TGAACTCCTG | CTGCTGGGAG | AGGCTGGATG | 1380 |
| GGTGGGAGAC | TGATGTTGAA | ACCAAAGAGC | TGGGCATCCA | GGCTTTTGGT | CACCATGGCA | 1440 |
| CTACCCCAAG | GCTTTTCCTG | TTCAGTGAGC | AGGAATTCAG | GATATAAGGA | GAAAACTGGG | 1500 |
| CTGAGATGCC | TGGTGGGCTT | TAGAGTAGGG | GCCCAGGATA | AGAGACAATG | AATTAATGAG | 1560 |
| GAGCATATGG | GGAAGGTGGC | TGAGGGTCCC | TGACTTACCT | TGACCCATGG | CTGAAGGCTC | 1620 |
| CATGCCCATG | GCTGGAGCTG | GGACCCTACA | CTTCTATAGT | CAAGGTGCTT | AGCCTCAAGG | 1680 |
| TTGCAGATGC | ACCCTCTAGT | ACTCTGGGTG | CAGACTGTAC | ACTGGGCGCA | GGGGGTTGTG | 1740 |
| GAAGGACAGT | GCAGATGATT | CTGGGCTTTT | GACACCACAG | TTCCCCAGG | GAAAGAGGCA | 1800 |
| CTACTAATAA | AAAC | | | | | 1814 |

( 2 ) INFORMATION FOR SEQ ID NO:2:

( i ) SEQUENCE CHARACTERISTICS:
( A ) LENGTH: 342 amino acids
( B ) TYPE: amino acid (D) TOPOLOGY: linear (ii) MOLECULE TYPE: protein (xi) SEQUENCE DESCRIPTION: SEQ ID NO:2:

| Met | Asn | Cys | Ile | Gly | Tyr | His | Pro | Thr | Arg | Arg | Leu | Arg | Ala | Trp | Gly |
| 1 | | | | 5 | | | | | 10 | | | | | 15 | |

| Gly | Leu | Ala | Gly | Gly | Ala | Thr | Phe | Met | Val | Ile | Trp | Phe | Phe | Trp | Leu |
| | | | 20 | | | | | 25 | | | | | 30 | | |

| Trp | Gly | Ser | Ala | Pro | Gly | Ser | Ala | Pro | Val | Pro | Gln | Ser | Thr | Leu | Thr |
| | | 35 | | | | | 40 | | | | | 45 | | | |

| Ile | Leu | Ile | Trp | His | Trp | Pro | Phe | Thr | Asn | Arg | Pro | Pro | Glu | Leu | Pro |
| | 50 | | | | | 55 | | | | | 60 | | | | |

| Gly | Asp | Thr | Cys | Thr | Arg | Tyr | Gly | Met | Ala | Ser | Cys | Arg | Leu | Ser | Ala |
| 65 | | | | | 70 | | | | | 75 | | | | | 80 |

| Asn | Arg | Ser | Leu | Leu | Ala | Ser | Ala | Asp | Ala | Val | Val | Phe | His | His | Arg |
| | | | | 85 | | | | | 90 | | | | | 95 | |

| Glu | Leu | Gln | Thr | Arg | Gln | Ser | Leu | Leu | Pro | Leu | Asp | Gln | Arg | Pro | His |
| | | | 100 | | | | | 105 | | | | | 110 | | |

| Gly | Gln | Pro | Trp | Val | Trp | Ala | Ser | Met | Glu | Ser | Pro | Ser | Asn | Thr | His |
| | | 115 | | | | | 120 | | | | | 125 | | | |

| Gly | Leu | His | Arg | Phe | Arg | Gly | Ile | Phe | Asn | Trp | Val | Leu | Ser | Tyr | Arg |
| | 130 | | | | | 135 | | | | | 140 | | | | |

| Arg | Asp | Ser | Asp | Ile | Phe | Val | Pro | Tyr | Gly | Arg | Leu | Glu | Pro | Leu | Ser |
| 145 | | | | | 150 | | | | | 155 | | | | | 160 |

| Gly | Pro | Thr | Ser | Pro | Leu | Pro | Ala | Lys | Ser | Arg | Met | Ala | Ala | Trp | Val |
| | | | | 165 | | | | | 170 | | | | | 175 | |

| Ile | Ser | Asn | Phe | Gln | Glu | Arg | Gln | Gln | Arg | Ala | Lys | Leu | Tyr | Arg | Gln |
| | | | 180 | | | | | 185 | | | | | 190 | | |

| Leu | Ala | Pro | His | Leu | Gln | Val | Asp | Val | Phe | Gly | Arg | Ala | Ser | Gly | Arg |
| | | 195 | | | | | 200 | | | | | 205 | | | |

| Pro | Leu | Cys | Ala | Asn | Cys | Leu | Leu | Pro | Thr | Leu | Ala | Arg | Tyr | Arg | Phe |
| | 210 | | | | | 215 | | | | | 220 | | | | |

| Tyr | Leu | Ala | Phe | Glu | Asn | Ser | Gln | His | Arg | Asp | Tyr | Ile | Thr | Glu | Lys |
| 225 | | | | | 230 | | | | | 235 | | | | | 240 |

| Phe | Trp | Arg | Asn | Ala | Leu | Ala | Ala | Gly | Ala | Val | Pro | Val | Ala | Leu | Gly |
| | | | | 245 | | | | | 250 | | | | | 255 | |

| Pro | Pro | Arg | Ala | Thr | Tyr | Glu | Ala | Phe | Val | Pro | Pro | Asp | Ala | Phe | Val |
| | | | 260 | | | | | 265 | | | | | 270 | | |

| His | Val | Asp | Asp | Phe | Ser | Ser | Ala | Arg | Glu | Leu | Ala | Val | Phe | Leu | Val |
| | | 275 | | | | | 280 | | | | | 285 | | | |

| Ser | Met | Asn | Glu | Ser | Arg | Tyr | Arg | Gly | Phe | Phe | Ala | Trp | Arg | Asp | Arg |
| | 290 | | | | | 295 | | | | | 300 | | | | |

| Leu | Arg | Val | Arg | Leu | Leu | Gly | Asp | Trp | Arg | Glu | Arg | Phe | Cys | Thr | Ile |
| 305 | | | | | 310 | | | | | 315 | | | | | 320 |

| Cys | Ala | Arg | Tyr | Pro | Tyr | Leu | Pro | Arg | Ser | Gln | Val | Tyr | Glu | Asp | Leu |
| | | | | 325 | | | | | 330 | | | | | 335 | |

| Glu | Ser | Trp | Phe | Gln | Ala |
| | | | 340 | | |

(2) INFORMATION FOR SEQ ID NO:3:

(i) SEQUENCE CHARACTERISTICS:
(A) LENGTH: 2134 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GGCACGCTGC | CTGTTCGCGC | CATGGGGCA | CCGTGGGGCT | CGCCGACGGC | GGCGGCGGGC | 60 |
| GGGCGGCGCG | GGTGGCGCCG | AGGCCGGGGG | CTGCCATGGA | CCGTCTGTGT | GCTGGCGGCC | 120 |
| GCCGGCTTGA | CGTGTACGGC | GCTGATCACC | TACGCTTGCT | GGGGGCAGCT | GCCGCCGCTG | 180 |
| CCTGGGCGTC | GCCAACCCCG | TCGCGACCGG | TGGGCGTGCT | GCTGTGGTGG | GAGCCCTTCG | 240 |
| GGGGCGCGAT | CAGCGCCCCG | AGGCCGCCCC | CTGACTGCCG | GCTGCGCTTC | AACATCAGCG | 300 |
| GCTGCCGCCT | GCTCACCGAC | ACGCGCGTCC | TACGGAGAGG | CTCAGGCCGT | GCTTTTCCAC | 360 |
| CACCGCGACC | TCGTGAAGGG | GCCCCCCGAC | TGGCCCCGC | CCTGGGCAT | CCAGGCGCAC | 420 |
| ACTGCCGAGG | AGGTGGATCT | GCGCGTGTTG | GACTACGAGG | AGGCAGCGGC | GGCGGCAGAA | 480 |
| GCCCTGGCGA | CCTCCAGCCC | CAGGCCCCGG | GCCAAGCGCT | GGGTTTGGAT | GAACTTCGAG | 540 |
| TCGCCCTCGC | ACTCCCCGGG | GCTGCGAAGC | CTGGCAAGTA | ACCTCTTCAA | CTGGACGCTC | 600 |
| TCCTACCGGG | CGGACTCGGA | CGTCTTTGTG | CCTTATGGCT | ACCTCTACCC | CAGAAGCCAC | 660 |
| CCCGGCGACC | CGCCCTCAGG | CCTGGCCCCG | CCACTGTCCA | GGAAACAGGG | GCTGGTGGCA | 720 |
| TGGGTGGTGA | GCCACTGGGA | CGAGCGCCAG | GCCCGGGTCC | GCTACTACCA | CCAACTGAGC | 780 |
| CAACATGTGA | CCGTGGACGT | GTTCGGCCGG | GGCGGGCCGG | GGCAGCCGGT | GCCCGAAATT | 840 |
| GGGCTCCTGC | ACACAGTGGC | CCGCTACAAG | TTCTACCTGG | CTTTCGAGAA | CTCGCAGCAC | 900 |
| CTGGATTATA | TCACCGAGAA | GCTCTGGCGC | AACGCGTTGC | TCGCTGGGGC | GGTGCCGGTG | 960 |
| GTGCTGGGCC | CAGACCGTGC | CAACTACGAG | CGCTTTGTGC | CCCGCGGCGC | CTTCATCCAC | 1020 |
| GTGGACGACT | TCCCAAGTGC | CTCCTCCCTG | GCCTCGTACC | TGCTTTTCCT | CGACCGCAAC | 1080 |
| CCCGCGGTCT | ATCGCCGCTA | CTTCCACTGG | CGCCGGAGCT | ACGCTGTCCA | CATCACCTCC | 1140 |
| TTCTGGGACG | AGCCTTGGTG | CCGGGTGTGC | CAGGCTGTAC | AGAGGGCTGG | GACCGGCCCA | 1200 |
| AGAGCATACG | GAACTTGGCC | AGCTGGTTCG | AGCGGTGAAG | CCGCGCTCCC | CTGGAAGCGA | 1260 |
| CCCAGGGGAG | GCCAAGTTGT | CAGCTTTTTG | ATCCTCTACT | GTGCATCTCC | TTGACTGCCC | 1320 |
| GCATCATGGG | AGTAAGTTCT | TCAAACACCC | ATTTTTGCTC | TATGGGAAAA | AAACGATTTA | 1380 |
| CCATTAATAT | TTACTCAGCA | CAGAGATGGG | GGCCCGGTTT | CCATATTTTT | TGCACAGCTA | 1440 |
| GCAATTGGGC | TCCCTTTGCT | GCTGATGGGC | ATCATTGTTT | AGGGGTGAAG | GAGGGGGTTC | 1500 |
| TTCCTCACCT | TGTAACCAGT | GCAGAAATGA | AATAGCTTAG | CGCAAGAAGC | CGTTGAGGCG | 1560 |
| GTTTCCTGAA | TTTCCCCATC | TGCCACAGGC | CATATTTGTG | GCCCGTGCAG | CTTCCAAATC | 1620 |
| TCATACACAA | CTGTTCCCGA | TTCACGTTTT | TCTGGACCAA | GGTGAAGCAA | ATTTGTGGTT | 1680 |
| GTAGAAGGAG | CCTTGTTGGT | GGAGAGTGGA | AGGACTGTGG | CTGCAGGTGG | GACTTTGTTG | 1740 |
| TTTGGATTCC | TCACAGCCTT | GGCTCCTGAG | AAAGGTGAGG | AGGGCAGTCC | AAGAGGGGCC | 1800 |
| GCTGACTTCT | TTCACAAGTA | CTATCTGTTC | CCCTGTCCTG | TGAATGGAAG | CAAAGTGCTG | 1860 |
| GATTGTCCTT | GGAGGAAACT | TAAGATGAAT | ACATGCGTGT | ACCTCACTTT | ACATAAGAAA | 1920 |
| TGTATTCCTG | AAAAGCTGCA | TTTAAATCAA | GTCCCAAATT | CATTGACTTA | GGGGAGTTCA | 1980 |
| GTATTTAATG | AAACCCTATG | GAGAATTTAT | CCCTTTACAA | TGTGAATAGT | CATCTCCTAA | 2040 |
| TTTGTTTCTT | CTGTCTTTAT | GTTTTTCTAT | AACCTGGATT | TTTTAAATCA | TATTAAAATT | 2100 |
| ACAGATGTGA | AAATAAAAAA | AAAAAAAAA | AAAA | | | 2134 |

( 2 ) INFORMATION FOR SEQ ID NO:4:

( i ) SEQUENCE CHARACTERISTICS:
 ( A ) LENGTH: 405 amino acids
 ( B ) TYPE: amino acid
 ( C ) STRANDEDNESS: Not Relevant
 ( D ) TOPOLOGY: linear ( i i ) MOLECULE TYPE: protein ( x i ) SEQUENCE DESCRIPTION: SEQ ID NO:4:

```
Met  Gly  Ala  Pro  Trp  Gly  Ser  Pro  Thr  Ala  Ala  Ala  Gly  Gly  Arg  Arg
 1                  5                        10                       15

Gly  Trp  Arg  Arg  Gly  Arg  Gly  Leu  Pro  Trp  Thr  Val  Cys  Val  Leu  Ala
            20                      25                       30

Ala  Ala  Gly  Leu  Thr  Cys  Thr  Ala  Leu  Ile  Thr  Tyr  Ala  Cys  Trp  Gly
           35                       40                       45

Gln  Leu  Pro  Pro  Leu  Pro  Trp  Ala  Ser  Pro  Thr  Pro  Ser  Arg  Pro  Val
      50                       55                       60

Gly  Val  Leu  Leu  Trp  Trp  Glu  Pro  Phe  Gly  Gly  Ala  Ile  Ser  Ala  Pro
 65                      70                       75                       80

Arg  Pro  Pro  Pro  Asp  Cys  Arg  Leu  Arg  Phe  Asn  Ile  Ser  Gly  Cys  Arg
                85                       90                       95

Leu  Leu  Thr  Asp  Arg  Ala  Ser  Tyr  Gly  Glu  Ala  Gln  Ala  Val  Leu  Phe
               100                      105                      110

His  His  Arg  Asp  Leu  Val  Lys  Gly  Pro  Pro  Asp  Trp  Pro  Pro  Pro  Trp
          115                      120                      125

Gly  Ile  Gln  Ala  His  Thr  Ala  Glu  Glu  Val  Asp  Leu  Arg  Val  Leu  Asp
     130                      135                      140

Tyr  Glu  Glu  Ala  Ala  Ala  Ala  Ala  Glu  Ala  Leu  Ala  Thr  Ser  Ser  Pro
145                      150                      155                      160

Arg  Pro  Arg  Ala  Lys  Arg  Trp  Val  Trp  Met  Asn  Phe  Glu  Ser  Pro  Ser
               165                      170                      175

His  Ser  Pro  Gly  Leu  Arg  Ser  Leu  Ala  Ser  Asn  Leu  Phe  Asn  Trp  Thr
               180                      185                      190

Leu  Ser  Tyr  Arg  Ala  Asp  Ser  Asp  Val  Phe  Val  Pro  Tyr  Gly  Tyr  Leu
               195                      200                      205

Tyr  Pro  Arg  Ser  His  Pro  Gly  Asp  Pro  Pro  Ser  Gly  Leu  Ala  Pro  Pro
210                      215                      220

Leu  Ser  Arg  Lys  Gln  Gly  Leu  Val  Ala  Trp  Val  Val  Ser  His  Trp  Asp
225                      230                      235                      240

Glu  Arg  Gln  Ala  Arg  Val  Arg  Tyr  Tyr  His  Gln  Leu  Ser  Gln  His  Val
               245                      250                      255

Thr  Val  Asp  Val  Phe  Gly  Arg  Gly  Gly  Pro  Gly  Gln  Pro  Val  Pro  Glu
               260                      265                      270

Ile  Gly  Leu  Leu  His  Thr  Val  Ala  Arg  Tyr  Lys  Phe  Tyr  Leu  Ala  Phe
          275                      280                      285

Glu  Asn  Ser  Gln  His  Leu  Asp  Tyr  Ile  Thr  Glu  Lys  Leu  Trp  Arg  Asn
     290                      295                      300

Ala  Leu  Leu  Ala  Gly  Ala  Val  Pro  Val  Val  Leu  Gly  Pro  Asp  Arg  Ala
305                      310                      315                      320

Asn  Tyr  Glu  Arg  Phe  Val  Pro  Arg  Gly  Ala  Phe  Ile  His  Val  Asp  Asp
               325                      330                      335

Phe  Pro  Ser  Ala  Ser  Ser  Leu  Ala  Ser  Tyr  Leu  Leu  Phe  Leu  Asp  Arg
               340                      345                      350

Asn  Pro  Ala  Val  Val  Arg  Arg  Tyr  Phe  His  Trp  Arg  Arg  Ser  Tyr  Ala
               355                      360                      365

Val  His  Ile  Thr  Ser  Phe  Trp  Asp  Glu  Pro  Trp  Cys  Arg  Val  Cys  Gln
```

|  |  |  |
|---|---|---|
| 370 | 375 | 380 |
| Ala Val Gln Arg Ala Gly Asp Arg Pro Lys Ser Ile Arg Asn Leu Ala | | |
| 385 390 395 400 | | |
| Ser Trp Phe Glu Arg | | |
| 405 | | |

FUCOSYLTRANSFERASE GENES AND USES THEREOF

STATEMENT AS TO FEDERALLY SPONSORED RESEARCH

This invention was made at least in part with funds from the Federal Government, and the Government therefore has certain rights in the invention.

BACKGROUND OF THE INVENTION

This invention relates to recombinant fucosyltransferases, DNA, and uses thereof.

The structurally related endothelial cell receptors E-selectin (Bevilacqua et al., Proc. Natl. Acad. Sci. USA 84:9238, 1987; Bevilacqua et al., Science 243:1160, 1989) and P-selectin (Hsu-Lin et al., J. Biol. Chem. 259:9121, 1984; Stenberg et al., J. Cell Biol. 101:880, 1985; Johnston et al., Blood 69:1401, 1987) mediate myeloid cell attachment to the vascular wall following activation of the endothelial cell by inflammatory cytokines (in the case of E-selectin; see, e.g., Bevilacqua et al. (1987), supra) or thrombin (in the case of P-selectin; see, e.g., Geng et al., Nature 343:757, 1990). Expressed both by Weibel-Palade bodies of endothelium (McEver et al., J. Clin. Invest. 84:920, 1989; Bonfanti et al., Blood 73:1109,.1989) and platelet alpha granules (Hsu-Lin et al., supra; Stenberg et al., supra), P-selectin also mediates monocyte and neutrophil binding to activated platelets (Larsen et al., Cell 59:305, 1989; Hamburger et al., Blood 75:550, 1990). The leading candidate ligands for the two receptors are the sialyl-Le$^x$ structure for E-selectin (Lowe et al., Cell 63:475, 1990; Phillips et al., Science 250:1130, 1990); Walz et al., Science 250:1132, 1990) and the same glycan in the context of a specific mucin, PSGL-1, (P-selectin glycoprotein ligand 1) for P-selectin (Sako et al., Cell 75:1179, 1993).

Genetic and biochemical data have demonstrated the existence of at least four distinct types of fucosyltransferases capable of forming the α(1,4) linkage: the Lewis enzyme (Fuc-TIII), which can transfer fucose either α(1,3) or α(1,4) to Galβ4GlcNAc or Galβ3GlcNAc respectively (Kukowska-Latallo et al., Genes Dev. 4:1288, 1990); at least one enzyme, Fuc-TIV, solely forming α(1,3) linkages, which cannot utilize sialylated substrates (Goelz et al., Cell 63:1349, 1989; Lowe et al., J. Biol. Chem. 266:17467, 1991); at least two enzymes, Fuc-TV (Weston et al., J. Biol. Chem. 267:4152, 1992a) and Fuc-TVI (Weston et al., J. Biol. Chem. 267:24575, 1992b) solely forming α(1,3) linkages, which can fucosylate either sialylated or nonsialylated precursors, and a recently described enzyme, Fuc-TVII, (Sasaki et al., J. Biol. Chem. 269:14730, 1994); Natsuka et al., J. Biol. Chem. 269:16789, 1994) which can fucosylate only sialylated precursors.

SUMMARY OF THE INVENTION

In general, the invention features substantially pure α(1,3) fucosyltransferase, including an amino acid sequence substantially identical to the sequence shown in FIG. 3 (SEQ ID NO: 2). In preferred embodiments, pure α(1,3) fucosyltransferase is obtained from a mammal (for example, a murine cell line (e.g., 32D c13), or from a human).

In a related aspect, the invention features a fragment or analog of α(1,3)fucosyltransferase polypeptide including an amino acid sequence substantially identical to the sequence shown in FIG. 3 (SEQ ID NO: 2).

In another related aspect, the invention features substantially pure DNA having a sequence substantially identical to the nucleotide sequence shown in FIG. 3 (SEQ ID NO: 1). In preferred embodiments, such DNA is cDNA or is genomic DNA. In related aspects, the invention also features a vector and a cell (e.g., a murine cell such as 32D c13 or a human cell such as human cell line 293) which includes such substantially pure DNA. In various preferred embodiments, the vector-containing cell is a prokaryotic cell, for example, E. coli, or, more preferably, is a eukaryotic mammalian cell (e.g., the murine cell line 32D c13 or human cell line 293).

In yet another related aspect, the invention features a method of fucosylating a polypeptide in vivo involving: (a) providing a cell containing the fucosyltransferase DNA of the invention including a nucleotide sequence which is substantially identical to the sequence shown in FIG. 3 (SEQ ID NO: 1) positioned for expression in the cell; and (b) culturing the transformed cell under conditions for expressing the DNA, resulting in the fucosylation of the protein.

In preferred embodiments, fucosylation occurs in a mammalian cell, for example, a human cell (e.g., human cell line 293) or a murine cell (e.g., 32D c13). In related aspects, the cell contains a second fucosyltransferase gene. Preferably, such a second gene is substantially identical to the nucleotide sequence shown in FIG. 6A (SEQ ID NO: 3) which encodes a polypeptide including an amino acid sequence substantially identical to the sequence shown in FIG. 6B (SEQ ID NO: 4). In preferred embodiments, the protein which is fucosylated according to the above method is an AGP-antibody fusion protein or is an antibody (e.g., IgG or IgM).

In another aspect, the invention features a recombinant polypeptide fucosylated using a cell expressing DNA which is substantially identical to the nucleotide sequence shown in FIG. 3 (SEQ ID NO: 1). Preferably, the fucosylated polypeptide is an AGP-antibody fusion protein, or is an antibody (e.g., IgG or IgM). In still other preferred embodiments, the polypeptide is further fucosylated using a second fucosyltransferase. Such a second fucosyltransferase is substantially identical to a polypeptide including an amino acid sequence shown in FIG. 6B (SEQ ID NO: 4). Preferably, the cell used to fucosylate the polypeptide is a mammalian cell (e.g., the murine cell line 32D c13 or the human cell line 293).

In another aspect, the invention features a polypeptide fucosylated in vitro using a fucosyltransferase having an amino acid sequence substantially identical to the sequence shown in FIG. 3 (SEQ ID NO: 2). In preferred embodiments, the fucosylated polypeptide is further fucosylated using a second fucosyltransferase. Such a second fucosyltransferase includes an amino acid sequence substantially identical to the sequence shown in FIG. 6B (SEQ ID NO: 4). Preferably, the fucosylated polypeptide is an AGP-antibody fusion protein or is an antibody (e.g., IgG or IgM).

In related aspects, the invention features a substantially pure polypeptide of the invention which is fucosylated in vivo or in vitro and which is capable of protecting a mammal against an adverse immune reaction. In general, such an adverse immune reaction is septic shock or is septicemia.

In another aspect, the invention features a cell containing at least two recombinant fucosyltransferases, one of the fucosyltransferases being substantially identical to the amino acid sequences shown in FIG. 3. (SEQ ID NO: 2) and another of the fucosyltransferases being substantially identical to the amino acid sequence shown in FIG. 6B (SEQ ID NO: 4). Preferably, such a DNA-containing cell is a prokaryotic cell (e.g., E. coli) or is a eukaryotic cell, for example, a mammalian cell (e.g., the murine cell line 32D c13 or human cell line 293).

In a final aspect, the invention features a method of fucosylating a polypeptide in vitro comprising: (a) providing an α(1,3) fucosyltransferase of the invention; and (b) contacting the polypeptide with the fucosyltransferase under conditions sufficient for fucosylating the polypeptide.

By "polypeptide" is meant any chain of amino acids, regardless of length or post-translational modification (e.g., glycosylation or phosphorylation).

By "substantially identical" is meant a polypeptide exhibiting at least 50%, preferably 70%, more preferably 90%, and most preferably 95% homology to a reference amino acid or is meant a nucleic acid sequence exhibiting at least 85%, preferably 90%, more preferably 95%, and most preferably 97% homology to a reference nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially pure polypeptide" is meant a fucosyltransferase polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, fucosyltransferase polypeptide. A substantially pure fucosyltransferase polypeptide may be obtained, for example, by extraction from a natural source (e.g., a murine cell such as 32D c13); by expression of a recombinant nucleic acid encoding a fucosyltransferase polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include, without limitation, those derived from eukaryotic organisms but synthesized in E. coli or other prokaryotes, or those derived from a eukaryotic cell which does not normally synthesize such a protein, or those derived from a eukaryotic cell engineered to overexpress such a protein.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a fucosyltransferase polypeptide.

By "positioned for expression" is meant that the DNA molecule is positioned adjacent to a DNA sequence which directs transcription and translation of the sequence (i.e., facilitates the production of, e.g., a recombinant fucosyltransferase polypeptide or RNA molecule).

By "promoter" is meant the minimal sequence sufficient to direct transcription. Also included in the invention are those promoter elements which are sufficient to render transcription controllable for cell-type specific, tissue-specific, or inducible expression; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a fucosyltransferase-specific antibody. A purified fucosyltransferase antibody may be obtained, for example, by affinity chromatography using recombinantly-produced fucosyltransferase protein or conserved motif peptides and standard techniques.

By "specifically binds" is meant an antibody which recognizes and binds a fucosyltransferase protein but which does not substantially recognize and bind other molecules in a sample, e.g., a biological sample, which naturally includes fucosyltransferase.

Other features and advantages of the invention will be apparent from the following description of the preferred embodiments thereof, and from the claims.

DETAILED DESCRIPTION

The drawings will first be described. Drawings

FIGS. 1A–1G are flow cytometry profile showing the expression of fucosylated glycans by COS cells transfected with murine myeloid fucosyltransferase. The results are expressed as mean fluorescence intensity in arbitrary units. No expression above background of any carbohydrate epitope except sialyl-Le$^x$ was seen.

Figure 2A:
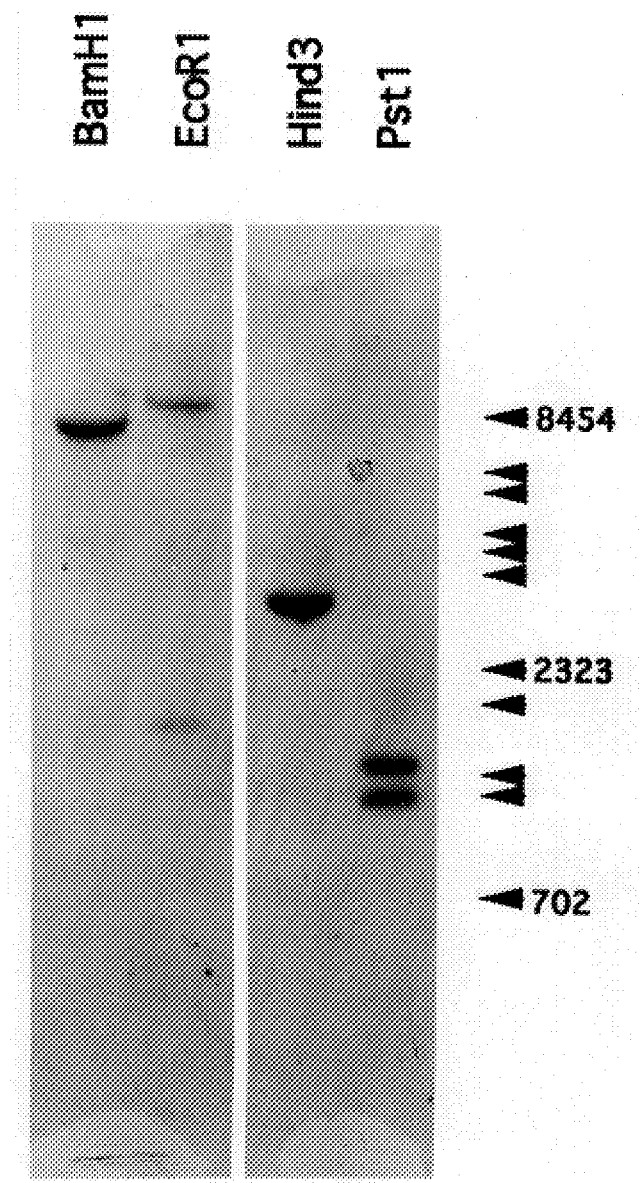
Figure 2B:
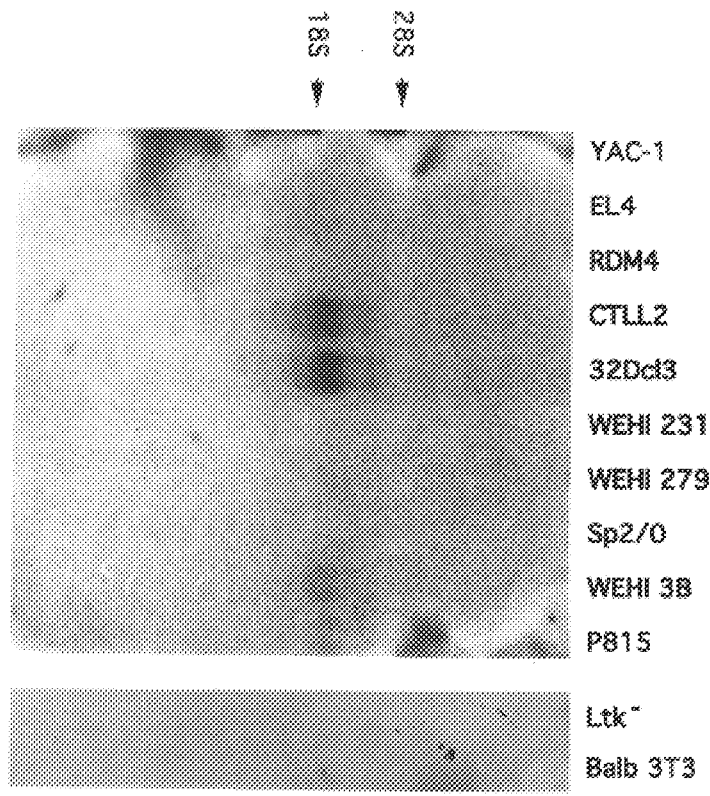
Figure 2C:
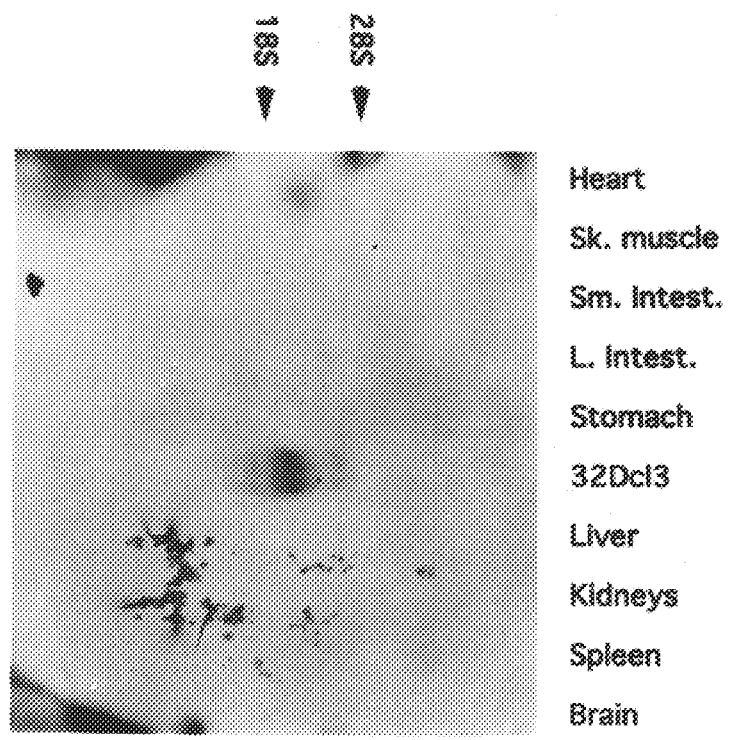

FIGS. 2A–2C is a panel of autoradiograms (A–C) showing different nucleic acid blot hybridizations. Panel (A) is an autoradiogram showing a DNA blot hybridization of total genomic DNA from mouse kidney tissue. Murine genomic DNA (15 μg) was digested with the indicated restriction enzymes and subjected to fractionation, transfer, and blot hybridization. Panel (B) is an autoradiogram showing an RNA blot hybridization of total RNA from different cell lines. Total RNA (20 μg) prepared from each of the cell lines shown was denatured, fractionated by gel electrophoresis, transferred to nylon and hybridized. The lineage origins of the cell lines are: YAC-1 (T cell leukemia), EL4 (thymoma), RDM4 (T cell leukemia), CTLL-2 (IL-2 dependent cytotoxic T cell), 32D c13 (IL-3 dependent granulocyte precursor), WEHI-231 (B cell lymphoma, non-secreting, mouse), WEHI-279 (B cell lymphoma, non-secreting, mouse), Sp2/0 (plasmacytoma), WEHI-3B (myeloid (monocytic) leukemia), P815 (mastocytoma), Ltk (fibroblast), and Balb 3T3 (fibroblast). Panel (C) is an autoradiogram showing an RNA blot hybridization of total RNA from skeletal tissue. Total RNA (20 μg) prepared from skeletal muscle (Sk. muscle) was denatured, fractionated by gel electrophoresis, transferred to nylon and hybridized. Arrows denote the location of ribosomal RNAs.

FIG. 3 is the nucleotide (SEQ ID NO: 1) and deduced amino acid sequence (SEQ ID NO: 2) of the murine myeloid-lineage fucosyltransferase cDNA. Two sites for N-linked glycan addition are underlined in the predicted peptide sequence, as is the upstream ATG in the nucleic acid sequence.

FIGS. 4A–4J are a flow cytometry profile showing the expression of fucosylated glycans by 32D c13 cells stably transfected with the human myeloid fucosyltransferase. Pooled products of the transfection of 32D c13 cells with a human Fuc-TIV myeloid fucosyltransferase expression plasmid bearing a selectable marker were evaluated by indirect immunofluorescence using anti-carbohydrate monoclonal antibodies and flow cytometry. The results are expressed as mean fluorescence intensity in arbitrary units.

Figure 5A:
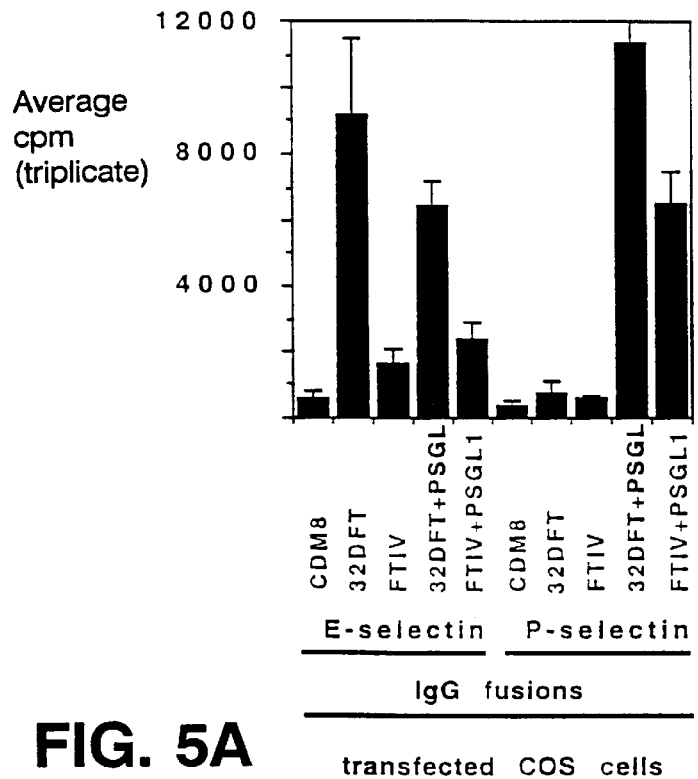
Figure 5B:
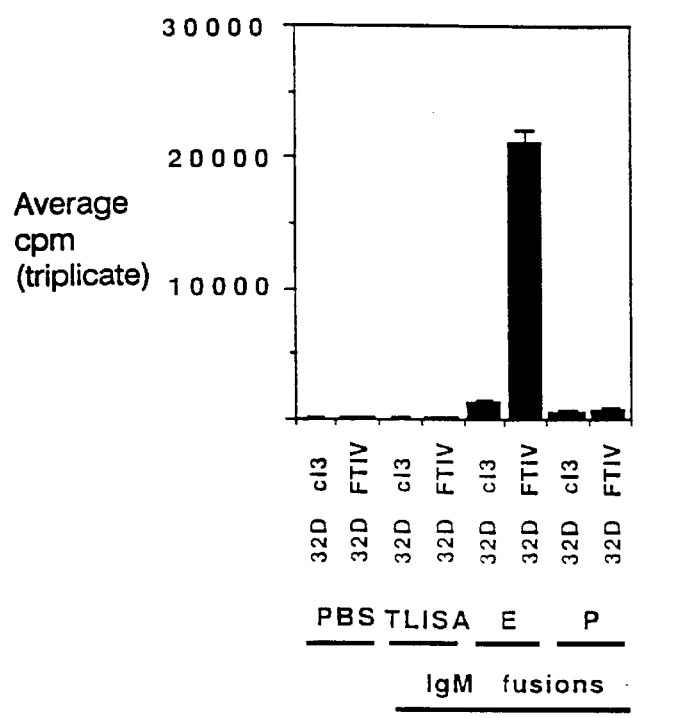

FIGS. 5A–5B are a bar graph of cell adhesion assays (Panels A–B). Panel (A) shows the adhesion to E-selectin or P-selectin IgG fusion proteins of COS cells transfected with either the human Fuc-TIV (FTIV) or the murine 32D c13 fucosyltransferase (32DFT) cDNAs in the presence or absence of the P-selectin glycoprotein ligand (PSGL). Panel (B) shows adhesion to E-selectin or P-selectin IgM fusion proteins of 32D c13 cells (32D c13) or 32D c13 cells transfected with the human myeloid Fuc-TIV cDNA (FTIV). TLISA, control IgM fusion protein; E, P, E- or P-selectin IgM fusion protein. Binding to P-selectin/IgM fusion protein was not significantly increased by expression of Fuc-TIV. Columns represent average cpm bound of triplicate samples.

FIGS. 6A–6B are is the nucleotide sequence (SEQ ID NO: 3) and, panel B, the deduced amino acid sequence (SEQ ID NO: 4) of the human myeloid-lineage Fuc-TIV cDNA.

Below we describe the isolation of an α(1,3) fucosyltransferase cDNA from a murine myeloid cell line which has a relatively strict substrate requirement for sialylated N-acetyllactosamine, which can account for the presence of the sialyl-Le$^x$ epitope on murine cells, and which is substantially more effective than the previously described myeloid cell fucosyltransferase, Fuc-TIV, in support of E-selectin-mediated COS cell adhesion. We also show that the introduction of the human Fuc-TIV transferase into a murine cell line results in the appearance of a fucosylated glycan pattern similar to that found on human neutrophils and monocytes. Murine cells expressing human Fuc-TIV show enhanced adhesion to E-selectin fusion proteins, indicating that Fuc-TIV has an important physiological function in the context of human granulocyte extravasation. These examples are presented to illustrate, not limit, the invention.

Cell Lines and Growth Conditions

The following cell lines and growth conditions were used in this study. YAC-1, EL4, RDM4, CTLL2, Sp2/0, WEHI-231, WEHI-279 and P815 cell lines were cultured in IMDM, 10% FCS, 50 mM mercaptoethanol, 50 U/ml penicillin and 50 μg/ml streptomycin. Balb 3T3, Ltk⁻ and COS-7 m6 cell lines were passaged in DMEM, 10% calf serum (CS) and 25 μg/ml gentamicin sulfate. The IL-3 producing, macrophage-like cell line WEHI-3B was cultured in RPMI-1640, 10% FCS, 50 U/ml penicillin and 50 mg/ml streptomycin. The IL-3 dependent mouse neutrophil progenitor cell line, 32D c13, was cultured in RPMI-1640, 10% FCS, 10% WEHI 3B-conditioned medium, 50 U/ml penicillin and 50 μg/ml streptomycin (Kreider et al., *Oncogene* 7:135, 1992).

Isolation of CDNA Encoding Murine α(1.3) Fucosyltransferase

To isolate a cDNA clone capable of directing the expression of sialyl-Le$^x$ determinants, an expression library was prepared from mRNA isolated from the murine cell line 32D c13, which phenotypically resembles a granulocyte precursor and which binds murine E- and P-selectin (Levinovitz et al., *J. Cell Blol.* 121:449, 1993) as follows. A cDNA library in the expression vector CDM8 was prepared from 32D c13 cells as described by Aruffo et al. (*Proc. Natl. Acad. Sci. USA* 84:8573, 1987) using the introduction of a Mung bean exonuclease treatment followed by T4 DNA polymerase prior to the addition BstX1 adaptors. Following the second strand synthesis, the CDNA pellet was resuspended in 225 μl distilled water, 25 μl 10X Mung bean incubation buffer (500 mM sodium acetate, 300 mM NaCl, 10 mM zinc sulfate, pH 5.0), and 10 U of Mung bean nuclease (New England Biolabs, Beverly, Mass.). After a 10 minute incubation period at 37° C., the reaction was stopped by adding 20 μl of 1 M Tris-HCl, pH 8.0 and 3 μl 0.5 M EDTA, pH 8.0. The cDNA was phenol extracted, ethanol precipitated and resuspended in 90 Al distilled H$_2$O. Following the addition of 10 μl 10x T4 DNA polymerase buffer (330 mM Tris acetate, 660 mNM potassium acetate, 100 mM magnesium acetate, 5 mM DTT, 1 mg/ml bovine serum albumin (BSA), pH 8.0), 1 μl of a mixture containing 25 mM each of the deoxynucleoside triphosphates and 1 U of T4 DNA polymerase (Boehringer-Mannheim), the mixture was incubated at 37° C. for 30 min. The reaction was stopped by adding 0.5 μl 0.5 M EDTA, phenol extracted and ethanol precipitated. Following ligation of the BstX1 adaptors, unligated adaptors were removed by repeated centrifugal ultrafiltration through a filter with a molecular weight cut off of 100 kD (Amicon, Danvers, Mass.), followed by velocity sedimentation fractionation.

The ligated cDNA in CDM8 was introduced into electro-competent MC1061/p3 cells by electroporation in 0.2 cm gap cuvettes (Bio-Rad laboratories, Hercules, Calif.) at a voltage of 2.5 kV, a capacitance of 25 μF and a parallel resistance of 400 Ohms. Transformed bacteria were plated on 20 dishes, 23×23 cm in size (Nunc, Denmark). Bacteria from each dish ($\approx$1.25×10$^5$ colonies) were harvested and an aliquot stored frozen at −70° C. in 40% glycerol. Plasmid DNA was isolated from each pool using a commercial kit (plasmid midi prep QIAGEN Inc., Chatsworth, Calif.) according to the manufacturer's recommendations.

The library was then divided into 20 pools of 1.25×10$^5$ cells each and between 200 and 500 ng of plasmid DNA from each of the 20 pools was separately transfected into COS-7 m6 cells at approximately 70% confluence in a 10 cm-dish using the DEAE-dextran method described by Seed et al. (*Proc. Natl. Acad. Sci USA* 84:3365, 1987). The COS cells were stained with the sialyl-Le$^x$ antibody and bacteria from positive pools replated at lower density. Between 48 and 60 hours post-transfection pools bearing cDNAs capable of directing the appearance of the sialyl-Le$^x$ determinant, dishes with positive cells were identified by immunocytochemistry using an anti-sialyl-Le$^x$ antibody (KM93, mouse IgM; Kamiya Biomedical Company, Thousand Oaks, Calif.), and an avidin-biotin complex protocol employing 9-amino-3-ethylcarbazol as a peroxidase substrate kit (Vector Labs, Burlingame, Calif.) essentially as described Horst et al. (*Nucleic Acids Res.* 19:4556, 1991; Vector Labs). Bacteria corresponding to positive pools were subsequently replated at lower density on 10 cm dishes. Plasmid DNA from these subpools was transfected into COS cells in 6 cm dishes. The procedure was repeated until a single plasmid was recovered that conferred binding of anti-sialyl-Le$^x$ antibody to transfected COS cells. Bacterial cells from the pool giving rise to the highest number of positive transfectants were plated at lower density on agar plates and DNA prepared from the bacteria was transfected into COS cells, allowing pools of successively less sequence complexity to be obtained until finally a single clonally pure plasmid isolate was shown to be capable of directing the appearance of the sialyl Lewis-X epitope in COS cells. Five out of twenty pools contained five or more positive cells.

Flow Cytometry Analysis

To confirm the expression of the sialyl Lewis-X epitope, we examined the expression of this epitope in COS cells transfected with the 32D c13 fucosyltransferase expression plasmid described above by indirect immunofluorescence using anti-carbohydrate monoclonal antibodies and flow cytometry as follows. Transfected COS cells to be stained for FACS analysis were harvested by detaching the cells from plates 48 to 60 hours post-transfection using 0.5 mM EDTA in phosphate-buffered saline (PBS). Staining of cells for FACS analysis was done by incubating 2×10$^6$ cells on ice for 20 to 30 minutes in 0.5 ml of 3% BSA in PBS with 4 $\mu$g/ml of antibody or in 0.5 ml of hybridoma supernatant for 20 to 30 minutes. For this analysis, the following antibodies were used: anti-Le$^x$ antibody (PM81, mouse IgM; Medarex, Inc., West Lebanon, N.H.), anti-sialyl-Le$^x$ (KM93, mouse IgM), anti-sialyl-Le$^a$ (KM231, mouse IgG1; Kamiya Biomedical Co., Thousand Oaks, Calif.), anti-Le$^a$ antibody (T174, mouse IgG1; Signet, Dedham, Mass.), anti-CD 65 (VIM-2) antibody (88H7, mouse IgM; AMAC, Westbrook, Me.), and the hybridoma secreting a mouse IgG3 antibody against di- and tri- fucosylated Le$^x$ (FHCR-1–2075/FH4; ATCC, Rockland, Md.). Following two washes in PBS, the cells were resuspended in 0.5 ml of 3% BSA in PBS containing 2 $\mu$g/ml FITC-conjugated anti-mouse IgG or IgM antibody (Organon Teknika Corp., Durham, N.C.). Washed cells were immediately analyzed by flow cytometry (Coulter Corp., Hialeah, Fla.) according to standard methods. Flow cytometric analysis of the transfected cells showed that sialyl-Le$^x$, but neither Le$^x$, CD65, di/trimeric Le$^x$ (FH4 epitope), Le$^a$, nor sialyl -Le$^a$ determinants could be detected (FIGS. 1A–1G).

DNA Blot (Southern) Hybridization Analysis

To determine gene copy number of the 32D c13 fucosyltransferase gene, DNA blot hybridization was performed as follows. Fifteen micrograms of mouse genomic DNA (Adult, male, Balb/c kidney; Clontech Labs, Palo Alto, Calif.) was digested overnight in a volume of 300 $\mu$l with 50 U of BamH1, 90 U of EcoR1, 100 U of HindIII and 100 U of PstI individually. The digests were phenol extracted, ethanol precipitated and separated on a 0.8% agarose gel. The gel was denatured by incubation in 0.5 M NaOH, 1.5 M NaCl, at room temperature for 30 minutes, briefly rinsed in distilled water, and neutralized for 30 minutes in 0.5 M Tris-HCl$_1$, pH 7.0, 1.5 M NaCl at room temperature. Following an incubation in 20X SSC for 30 minutes, the DNA was blotted and probed as for the RNA blots described below. The results of this analysis indicated that the fucosyltransferase is encoded by at least a single copy gene (FIG. 2A).

RNA Blot Hybridization Analysis

To study the expression of the 32D c13 fucosyltransferase gene, RNA blot hybridization was performed as follows. Total RNA was isolated from YAC-1, EL4, RD-M4, CTLL2, 32D c13, WEHI 231, WEHI 279, Sp2/0, WEHI 3B, P815, Ltk- and Balb 3T3 cells using a guanidinium-acid phenol protocol (Chomczynski et al., *Analyt. Biochem.* 162:156, 1987). The heart, stomach, small intestine, large intestine, liver, kidneys, spleen, brain and a piece of skeletal muscle was dissected from a male 129 SVJ mouse sacrificed by cervical dislocation. Total RNA was isolated from the tissues as described above after homogenization on ice in guanidinium thiocyanate buffer using a handheld homogenizer (Omni International, Waterbury, Conn.). Twenty micrograms of total RNA was separated by electrophoresis in a 1.2% agarose/formaldehyde gel and transferred to nylon membranes (Schleicher & Schuell, Keene, N.H.) using a downward transfer system (Schleicher & Schuell) according to the manufacturer's recommendations. RNA absorbed to the membrane was crosslinked by UV irradiation (1200 $\mu$J) and detected by hybridization with a randomly primed probe using standard conditions (Ausubel et al., *Current Protocols In Molecular Biology*, Wiley Interscience, 1995).

RNA blot analysis showed a pattern of highly tissue-restricted expression of a message of 1.9 kb (FIG. 2 B and C). Among established cell lines high levels of mRNA were found in 32D c13 and CTLL-2, an IL-2 dependent cytotoxic T cell line, with the myeloid cell line WEHI 3B and the mastocytoma P815 having significant quantities of the mRNA (FIG. 2B). No message was detected in T-cell lines (YAC-1, EL4 and RDM4), in B cell or fibroblast lines, or in any of the tissues sampled (FIG. 2B).

DNA Sequencing

The sequence of the isolated cDNA clone was determined by the dideoxy chain termination method using modified T7 DNA polymerase (U.S. Biochemical Corp., Cleveland, Ohio) (Sanger et al., *Proc. Natl. Acad. Sci. USA* 74:5463, 1977). Ambiguities found in the sequence due to self-complementary sequences were resolved using 7-deasa-dGTP.

DNA Sequence Analysis and Deduced Protein Sequence

The cDNA insert consists of 1814 nucleotides, terminating just 3' to a canonical upstream poly(A) sequence motif (FIG. 3). The largest open reading frame begins at a methionine at position 325 which does not meet the sequence requirements for a translational initiation consensus, but is preceded by only one other candidate ATG, similarly lacking a consensus initiation context and giving rise to a translation product which terminates within a few residues. The predicted polypeptide contains a long amino-terminal hydrophobic region preceded by arginine residues, similar in structure to the transmembrane domain of type II (amino terminally anchored) integral membrane proteins typical of this class of glycosyltransferase. A carboxylterminal sequence from peptide residues 245 to 258 consisting largely of aliphatic hydrophobic amino acids, although reminiscent of the membrane spanning domains of type I integral membrane proteins, is probably too short to serve a membrane insertion function. The predicted molecular mass of the encoded protein is 39.4 kilodaltons, with the presence of two N-linked glycan addition sites at residues 81 and 291 suggesting that the mature protein may be larger.

Comparison of protein sequences showed that the 32D c13 fucosyltransferase shares identity at 47% of residues with the human myeloid fucosyltransferase and at 80% of residues with the human type VII fucosyltransferase. Given that the N-acetyllactosamine fucosyltransferases constitute a large and growing family, it is likely that another unidentified human isolate may prove more closely related to the present 32D c13 fucosyltransferase enzyme. Such a gene is isolated using the techniques described herein.

Expression of Human Fucosyltransferase in Murine Cells

The cDNA insert of a previously isolated expression clone encoding human myeloid α(1,3) fucosyltransferase (Fuc-TIV; FIG. 6A–6B, SEQ ID NO: 3) was excised from the πH3m vector (Aruffo et al. *Proc. Natl. Acad. Sci. USA* 84:8573, 1987) with HindIII and HpaI and subcloned into the polylinker of a bidirectional vector bearing the Spleen-focus forming virus (Sffv) LTR upstream of a polylinker, a splice donor and acceptor site, and the bidirectional poly(A) addition signal from SV40; opposite in orientation to this transcription unit, and utilizing the poly(A) signals from the opposite direction was a second transcription unit consisting of the HSV TK promoter followed by the coding sequences for puromycin acetyltransferase. The Sffv Fuc-TIV plasmid was linearized by digestion with Avr2, phenol extracted, ethanol precipitated, and electroporated into the 32D c13 cell line as follows. The cells ($8\times10^7$) were resuspended in 0.8 ml RPMI-1640, 10% FBS, 10% WEHI-3B conditioned medium, and transferred together with 40 μg of linearized plasmid DNA to a 0.4 cm-gap electroporation cuvette (Bio-Rad, Hercules, Calif.) on ice. A single pulse was delivered at a voltage of 250 V and a capacitance of 500 μF. After electroporation, the cuvette was put back on ice for 10 minutes before the cells were transferred to a flask containing 50 ml of medium. Puromycin was added to the medium the following day at a concentration of 0.5 μg/ml. After approximately 2 weeks, with media changes every second to third day, the cells were checked for expression of the sialyl-Le$^x$ epitope.

Transfection of the human myeloid cell-specific fucosyltransferase cDNA (Fuc-TIV; FIG. 6A–6B, SEQ ID NO: 3) into a murine granulocytic cell line resulted in the appearance of glycan epitope pattern similar to that of human cells (FIG. 4A–4J). Specifically, the levels of expression of Le$^x$ (CD15) and NeuNAcα3Galβ4GlcNAcβ3Galβ4(Fucα3)GlcNAc (CD65) epitopes were markedly increased, and substantial levels of multiply fucosylated poly N-acetyllactosamine epitopes were also detected. Together these findings support the notion that internally fucosylated poly N-acetyllactosamine chains are present in the transfectant but not parental cells.

Fusion Proteins

The construction of DNA sequences coding for fusions between E- and P-selectin extracellular domains (for P-selectin only 2 of the complement regulatory domains were included) and the Fc part (hinge, CH2 and CH3) of human genomic IgG1 was performed as previously described (Walz et al., *Science* 250:1132, 1990; Aruffo et al., *Cell* 61:1303, 1990). The cDNA sequences for E- and P-selectin extracellular domains were fused to the genomic sequence of human IgM Fc (CH2, CH3 and CH4) by transferring the selectin sequences from an IgG fusion vector to an IgM fusion vector created in this laboratory (Zettlmeissl et al., DNA Cell Biol. 9:347, 1990). The PSGL-1 cDNA coding sequence was obtained by PCR from an HL-60 cDNA library and confirmed by DNA sequencing. The coding segment for the mature extracellular, transmembrane and intracellular domain was inserted in an expression vector based on CDM8 which lacks the polyoma virus origin of replication and contains the leader sequence for the CD5 antigen positioned just upstream of the coding region for an influenza hemagglutinin peptide epitope tag.

COS cell supernatants containing soluble E- and P-selectin/IgG and IgM fusion proteins were produced as previously described (Walz et al., *Science* 250:1132, 1990; Aruffo et al., *Cell* 61:1303, 1990). The concentration of fusion protein in the tissue culture supernatants was determined by a 96-well ELISA assay, in which the fusion proteins were captured with an affinity purified, polyclonal anti-human IgG Fc or anti-human IgM (μ chain specific) antibody (Organon Teknika, Durham, N.C.). Captured fusion proteins were detected with a peroxidase-conjugated, affinity purified, polyclonal anti-human IgG Fc or anti-human IgM (μ chain specific) antibody (Organon Teknika) using 0-phenylenediamine dihydrochloride as substrate (Sigma). The ELISA was calibrated using purified human IgG or IgM (Sigma).

Adhesion Assays

Adhesion assays were performed in 96-well ELISA plates (Becton-Dickinson, Oxnard, Calif.) as follows. The wells were incubated with 100 μl of 20 μ/ml anti-human IgG Fc or anti-human IgM (heavy chain specific) in PBS for 2 hrs in a humid chamber at room temperature. After washing the plate twice with PBS, additional protein-binding sites were blocked by an overnight incubation with 200 μl 3% BSA in PBS. The plate was washed with PBS four times and incubated with 200 μl of fusion protein supernatants for 2 hrs. Following three PBS washes and one wash in 0.2% BSA, 0.15 M NaCl, 3 mM CaCl$_2$, $2\times10^5$ cells/well in 200 μl 0.2% BSA, 0.15 M NaCl, 3 mM CaCl$_2$ were added and left to bind for 15 minutes in room temperature having the plate on a rotary platform (60 rpm). The plate was washed three times by carefully dropping in 200 μl 0.15 M NaCl, 3 mM CaCl$_2$ in the wells and then carefully inverting the plate on a pile of paper towels in order to gently pour out the liquid. Transfected cells used for the assay were lifted off the dish with 0.5 mM EDTA in PBS 48 to 60 hrs after transfection and loaded with 100 μl Na$_2$$^{51}$CrO$_4$ (1 mCi/ml; DuPont, Boston, Mass.) in 0.9% NaCl plus 100 ml medium at 37° C. for 1 hr. Loaded cells were washed twice in PBS and resuspended in 0.2% BSA, 0.15 M NaCl, 3 mM CaCl$_2$. Adherent cells were lysed by the addition of 200 μl 2% SDS and counted in a gamma ray spectrometer.

The results of these experiments showed that COS cells transfected with the 32D c13 fucosyltransferase CDNA had significantly greater binding to immobilized E- and P-selectin than did the human Fuc-TIV (myeloid) enzyme; the binding to P-selectin was observed only when the COS cells were cotransfected with a CDNA expression vector encoding PSGL-1 (FIG. 5A).

The 32D c13 cell line itself binds both human E- and P-selectin/IgM fusion proteins (FIG. 5B). IgM fusion proteins were used in these experiments to avoid the possible contribution of Fc receptor binding. To evaluate the functional consequences of a human-like fucosylated glycan spectrum, 32D c13 cells stably expressing the human Fuc-TIV (myeloid) enzyme (FIG. 6B) were evaluated in the selectin adhesion assay. The transfectants showed an approximately 10-fold higher binding density to human E-selectin relative to untransfected cells, whereas binding to P-selectin was not significantly affected (FIG. 5A–5D).

Isolation of Fucosyltransferase cDNA and Genomic DNA

Cloning and isolation of fucosyltransferase cDNA according to the invention is carried out according to the methods described herein. Cloning of genomic DNA is performed according to well known methods.

Based on our discovery of a novel myeloid-expressed fucosyltransferase, the isolation of additional mammalian fucosyltransferases, including human fucosyltransferases, is made possible using standard techniques. In particular, using all or a portion of the amino acid sequence of a fucosyltransferase of the invention, one may readily design fucosyltransferase oligonucleotide probes, including fucosyltransferase degenerate oligonucleotide probes (i.e., a mixture of all possible coding sequences for a given amino acid sequence). These oligonucleotides may be based upon the sequence of either strand of the DNA comprising the motif. General methods for designing and preparing such probes are provided, for example, in Ausubel et al., supra, and *Guide to Molecular Cloning Techniques*, 1987, S. L. Berger and A. R. Kimmel, eds., Academic Press, New York. These oligonucleotides are useful for fucosyltransferase gene isolation, either through their use as probes capable of hybridizing to fucosyltransferase complementary sequences or as primers for various polymerase chain reaction (PCR) cloning strategies. In one particular example, isolation of other fucosyltransferase genes is performed by PCR amplification techniques well known to those skilled in the art of molecular biology using oligonucleotide primers designed to amplify only sequences flanked by the oligonucleotides in genes having sequence identity to fucosyltransferase of the invention. The primers are optionally designed to allow cloning of the amplified product into a suitable vector.

Hybridization techniques and procedures are well known to those skilled in the art and are described, for example, in Ausubel et al., supra, and *Guide to Molecular Cloning Techniques*, supra. If desired, a combination of different oligonucleotide probes may be used for the screening of the recombinant DNA library. The oligonucleotides are labelled with 32p using methods known in the art, and the detectably-labelled oligonucleotides are used to probe filter replicas from a recombinant DNA library. Recombinant DNA libraries may be prepared according to methods well known in the art, for example, as described in Ausubel et al., supra, or may be obtained from commercial sources.

For detection or isolation of closely related fucosyltransferases, high stringency conditions may be used; such conditions include hybridization at about 42° C. and about 50% formamide; a first wash at about 65° C., about 2X SSC, and 1% SDS; followed by a second wash at about 65° C. and about 0.1% SDS, 1X SSC. Lower stringency conditions for detecting fucosyltransferase genes having about 85% sequence identity to the fucosyltransferase gene described herein include, for example, hybridization at about 42° C. in the absence of formamide; a first wash at about 42° C, about 6X SSC, and about 1% SDS; and a second wash at about 50° C., about 6X SSC, and about 1% SDS.

As discussed above, fucosyltransferase oligonucleotides may also be used as primers in PCR cloning strategies. Such PCR methods are well known in the art and described, for example, in *PCR Technology*, H. A. Erlich, ed., Stockton Press, London, 1989; *PCR Protocols: A Guide to Methods and Applications*, M. A. Innis, D. H. Gelfand, J. J. Sninsky, and T. J. White, eds., Academic Press, Inc., New York, 1990; and Ausubel et al., supra. If desired, fucosyltransferases may be isolated using the PCR "RACE" technique, or Rapid Amplification of cDNA Ends (see, e.g., Innis et al., supra). By this method, oligonucleotide primers based on a fucosyltransferase conserved domain are oriented in the 3' and 5' directions and are used to generate overlapping PCR fragments. These overlapping 3'-and 5'-end RACE products are combined to produce an intact full-length cDNA. This method is described in Innis et al., supra; and Frohman et al., *Proc. Natl. Acad. Sci. USA* 85:8998, 1988.

Fucosyltransferase Polypeptide Expression

Fucosyltransferases according to the invention may be expressed or produced by transformation of a suitable host cell with all or part of a fucosyltransferase-encoding cDNA fragment (e.g., the CDNA described herein) in a suitable expression vehicle (e.g., those described herein).

Those skilled in the field of molecular biology will understand that any of a wide variety of expression systems may be used to provide the recombinant protein. For example, a fucosyltransferase may be produced in a prokaryotic host (e.g., *E. coli*) or in a eukaryotic host (e.g., Saccharomyces cerevisiae or mammalian cells, e.g., 32D c13, human cell line 293, COS 1, NIH 3T3, and JEG3 cells). Such cells are available from a wide range of sources (e.g., the American Type Culture Collection, Rockland, Md.; also, see, e.g., Ausubel et al., supra). The method of transformation and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a fucosyltransferase polypeptide is inserted into the pMAMneo vector in an orientation designed to allow expression. The recombinant fucosyltransferase is isolated as described below. Other preferable host cells which may be used in conjunction with the pMAMneo expression vehicle include COS cells and CHO cells (ATCC Accession Nos. CRL 1650 and CCL 61, respectively).

More preferably, fucosyltransferase of the invention is expressed or produced by a stably-transfected mammalian cell line (e.g., 32D c13, or human cell line 293) using the methods and vectors described herein.

In addition, a number of other vectors suitable for stable transfection of mammalian cells are available to the public, e.g., see Pouwels et al. (supra); methods for constructing such cell lines are also publicly available, e.g., in Ausubel et al. (supra). In one example, cDNA encoding the fucosyltransferase polypeptide is cloned into an expression vector which includes the dihydrofolate reductase (DHFR) gene. Integration of the plasmid and, therefore, the fucosyltransferase-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR⁻cells, ATCC Accession No. CRL 9096) are among the host cells preferred for DHFR selection of a stably-transfected cell line or DHFR-mediated gene amplification.

Once the recombinant fucosyltransferase polypeptide is expressed, it is isolated, e.g., using affinity chromatography. In one example, an anti-fucosyltransferase antibody (e.g., produced as described below) may be attached to a column and used to isolate the polypeptide. Lysis and fractionation of fucosyltransferase-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

These general techniques of polypeptide expression and purification can also be used to produce and isolate useful fucosyltransferase fragments or analogs (described below).

Identification of Molecules

Which Modulate Fucosyltransferase Expression

Isolation of the fucosyltransferase gene also facilitates the identification of molecules which increase or decrease fucosyltransferase expression, and which are therefore useful as therapeutics, e.g., for treatment of inflammation. According to one approach, candidate molecules (e.g., peptide or non-peptide molecules found, e.g., in a cell extract, mammalian serum, or growth medium on which mammalian cells have been cultured, or oligonucleotides) are added at varying concentrations to the culture medium of cells which express fucosyltransferase MRNA (e.g., 32D c13). Fucosyltransferase expression is then measured by standard Northern blot analysis (Ausubel et al., supra) using fucosyltransferase cDNA as a hybridization probe. The level of fucosyltransferase expression in the presence of the candidate molecule is compared to the level measured for the same cells in the same culture medium but in the absence of the candidate molecule. A molecule which promotes an increase or decrease in fucosyltransferase expression is considered useful in the invention.

Anti-Fucosyltransferase Antibodies

Fucosyltransferases described herein (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the fucosyltransferase polypeptides described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific fucosyltransferase recognition by Western blot or immunoprecipitation analysis (by the methods described in Ausubel et al., supra). Antibodies which specifically recognize fucosyltransferase are considered to be useful in the invention; such antibodies may be used, e.g., in an immunoassay to monitor the level of fucosyltransferase produced by a mammal.

Fucosylation and Production of Sialyl-Le$^x$
Determinants

The invention features genes, enzymes, and methods for fucosylating virtually any protein bearing one or more glycan addition sites, e.g., an N-linked glycan addition site. By "N-linked" is meant bonded to the amide nitrogen of an asparagine residue of a protein. For example, it has been discovered that antibodies (as described in Seed et al., USSN 08/402,888, entitled "AGP-Antibody Fusion Proteins and Related Molecules and Methods," filed Jun. 7, 1995) bearing one or more genetically-engineered carbohydrate determinants mask the CH2 portion of the immunoglobulin molecule and thus inhibit complement fixation and $F_c$ receptor binding. Such antibodies are useful for disrupting undesirable interactions between cells or proteins, or, generally, for disrupting an interaction between any two molecules, one of which bears a determinant specifically recognized by an antibody. Because the carbohydrate moieties block the immunoglobulin domain which triggers complement fixation and $F_c$ receptor binding, such antibodies do not elicit the undesirable side effects (i.e., those resulting from complement fixation and Fc receptor binding) frequently associated with antibody-based therapies. Preferably, the carbohydrate groups serve not only to inhibit undesirable complement fixation and Fc receptor binding, but also perform the function of competitively inhibiting a carbohydrate ligand-cell adhesion protein interaction. Where the carbohydrate groups perform this function, the antibody generally does not serve any function arising from its specificity, but serves only as a carrier for the carbohydrate groups. There is described herein such a molecule, in which the carbohydrate side chain includes the sialyl-Le$^x$ determinant.

Sialyl-Le$^x$ normally acts to facilitate interaction between cells which bear it (e.g., neutrophils) and cells which bear the protein, ELAM-1 or E-selectin (e.g., endothelial cells, e.g., those lining the blood vessel walls). Disrupting this interaction has therapeutic applications, for example, in minimizing inflammation, such as that which occurs following tissue injury, e.g., myocardial infarction, which is characteristic of diseases such as psoriasis or rheumatoid arthritis, or for preventing or inhibiting septicemia or septic shock which is induced by a microbial- or host-mediated immune reaction.

According to one example, the gene encoding a protein bearing a sialyl-Le$^x$ determinant, e.g., an IgG1 antibody or an $\alpha_1$-AGP-antibody fusion, is inserted into a vector designed to express the protein in a eukaryotic cell (see, e.g., those vectors described in Gillies et al., U.S. Pat. No. 4,663,281, hereby incorporated by reference). The eukaryotic host cell is preferably a mammalian cell (e.g., 32D c13, or human cell line 293, or a CHO, or lec11 cell), and the expression vector containing the sialyl-Le$^x$- encoding sequence is introduced into the host cell by transient or stable transfection using standard techniques. Such host cells are also transfected (transiently or stably) with a vector capable of expressing an α(1,3)fucosyltransferase of the invention (i.e., an enzyme capable of attaching one or more sialyl-Le$^x$ groups to the protein molecule at sialyl-Le$^x$ consensus glycosylation sites (N-X-T/S)). The α(1,3) fucosyltransferase gene described herein or a combination of the α(1,3)fucosyltransferase gene described herein and the Fuc-TIV gene may be expressed from a vector distinct from that encoding the protein containing sialyl-Le$^x$ addition sites, or, if desired, the genes may be carried on, and expressed from, a common vector. Mammalian cells are particularly useful hosts for the synthesis of sialyl-Le$^x$ modified proteins because they provide all required precursors for sialyl-Le$^x$ production.

Proteins (e.g., antibodies, AGP, or AGP-antibody fusions) which are fucosylated according to the methods of the invention have important therapeutic and diagnostic uses. Previous work has demonstrated that large amounts of antibody fusion proteins may be generated and secreted transiently from transfected mammalian cells (for example, COS cells). In general, to produce an antibody fusion protein, cDNA encoding a domain of interest is fused in-frame, for example, to human IgG domains (for example, constant domains) by standard techniques, and the fusion protein is expressed. The antibody portion of the molecule facilitates fusion protein purification and also prolongs the plasma half-life of otherwise short-lived polypeptides or polypeptide domains. Recombinant plasmids expressing $\alpha_1$-AGP-IgG1 fusion proteins (e.g., $\alpha_1$-AGP-Hinge-CH2-CH3 and $\alpha_1$-AGP-CH2-CH3) are disclosed in Seed et al., USSN 08/472,888, entitled "AGP-Antibody Fusion Proteins and Related Molecules and Methods," filed Jun. 7, 1995.

Host cells expressing the α(1,3)fucosyltransferase of the invention or a combination of any α(1,3)fucosyltransferase of the invention and Fuc-TIV (e.g., SEQ ID NO: 4) along with a protein which is to be fucosylated, e.g., IgG1 or an AGP-antibody fusion, are grown by standard methods and the fucosylated protein purified by standard techniques (for example, for an antibody or antibody fusion protein, using a Protein A column).

Alternatively, any protein, e.g., IgG1 or an AGP-antibody fusion, bearing sialyl-Le$^x$ addition sites may be fucosylated in vitro using any of the enzymes or any combination of enzymes described herein according to standard methods known in the art. Again, such in vitro fucosylated proteins can be purified using any standard technique of isolation and purification.

Fucosyltransferase Kits

Kits for carrying out any of the methods disclosed herein are also included in the invention. Such kits generally include a gene encoding the α(1,3)fucosyltransferase of the invention (for example, a fucosyltransferase gene encoding a polypeptide including an amino acid sequence substantially identical to the amino acid sequence shown in FIG. 3; SEQ ID NO: 2). Such a kit may also include a gene encoding Fuc-TIV (for example, a human Fuc-TIV polypeptide including an amino acid sequence substantially identical to the amino acid sequence shown in FIG. 6C; SEQ ID NO: 4) and/or a cell useful for expressing one or more fucosyltransferase genes. Alternatively, a kit according to the invention may include a transformed cell harboring an α(1,3) fucosyltransferase gene described herein, optionally in combination with a Fuc-TIV-encoding gene. Preferably, such fucosyltransferases are expressed in the 32D c13 cell line or human cell line 293. For identifying modulators of the fucosyltransferases described herein, a kit may include a fragment of an α(1,3)fucosyltransferase nucleic acid sequence useful for hybridization purposes, and may also include means for detecting and quantitating α(1,3) fucosyltransferase RNA hybridization.

Other kits according to the invention include substantially pure α(1,3)fucosyltransferase polypeptide (for example, a fucosyltransferase polypeptide including an amino acid sequence substantially identical to the amino acid sequence shown in FIG. 3; SEQ ID NO: 2). Such a kit may also include substantially pure Fuc-TIV polypeptide (for example, a fucosyltransferase polypeptide including an amino acid sequence substantially identical to the amino acid sequence shown in FIG. 6C; SEQ ID NO: 4). Such fucosyltransferase kits are useful for fucosylating a molecule in vitro.

Other Embodiments

Polypeptides according to the invention include the entire murine fucosyltransferase sequence (as shown in FIG. 3; SEQ ID NO: 2) as well as any analog or fragment of the murine fucosyltransferase.

Polypeptides of the invention also include all mRNA processing variants (e.g., all products of alternative splicing or differential promoter utilization) as well as analogous fucosyltransferases from other mammals, including humans.

Specific fucosyltransferase fragments or analogues of interest include full-length or partial (see below) proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy enzymatic activity (as assayed above or according to any other standard method). Analogs also include fucosyltransferase polypeptides which are modified for the purpose of increasing peptide stability; such analogs may contain, e.g., one or more desaturated peptide bonds or D-amino acids in the peptide sequence or the peptide may be formulated as a cyclized peptide molecule.

Other embodiments are within the following claims.

What is claimed is:

1. A substantially pure $\alpha_1$-acid glycoprotein (AGP) or AGP fusion polypeptide which has been fucosylated using a cell expressing substantially pure DNA having a sequence substantially identical to the nucleotide sequence shown in FIG. 3 (SEQ ID NO: 1), wherein said polypeptide is capable of protecting a mammal against an LPS-induced adverse immune reaction.

2. The polypeptide of claim 1, wherein said adverse immune reaction is septic shock.

3. The polypeptide of claim 1, wherein said adverse immune reaction is septicemia.

4. A substantially pure AGP or AGP fusion polypeptide fucosylated in vitro using a fucosyltransferase having an amino acid sequence substantially identical to the sequence shown in FIG. 3 (SEQ ID NO: 2), wherein said polypeptide is capable of protecting a mammal against an LPS-induced adverse immune reaction.

5. The polypeptide of claim 4, wherein said adverse immune reaction is septic shock.

6. The polypeptide of claim 4, wherein said adverse immune reaction is septicemia.

7. The polypeptide of claim 1, wherein said polypeptide is fucosylated using a cell expressing DNA which encodes the amino acid sequence of SEQ ID NO: 2.

8. The polypeptide of claim 1, wherein said polypeptide is fucosylated using a cell expressing DNA having the nucleotide sequence of SEQ ID NO: 1.

9. The polypeptide of claim 4, wherein said polypeptide is fucosylated in vitro using a fucosyltransferase having the amino acid sequence of SEQ ID NO: 2.

10. The polypeptide of claim 1 or claim 4, wherein said fucosylated polypeptide is an AGP-antibody fusion protein.

11. The polypeptide of claim 1 or claim 4, wherein said fucosylated polypeptide is an antibody protein.

12. The polypeptide of claim 11, wherein said antibody is IgG.

* * * * *

UNITED STATES PATENT AND TRADEMARK OFFICE
CERTIFICATE OF CORRECTION

PATENT NO. : 5,858,752
DATED : Jan. 12, 1999
INVENTOR(S) : Brian Seed and Jan Holgersson Page 1 of 2

It is certified that error appears in the above-identified patent and that said Letters Patent is hereby corrected as shown below:

At col. 6, line 36, replace "mNM" with --mM--.

At col. 10, line 36, replace "μ/ml" with --μg/ml--.

At col. 10, line 60, replace "CDNA" with --cDNA--.

At col. 10, line 64, replace "CDNA" with --cDNA--.

At col. 11, line 5, replace "FIG. 6B" with --FIG. 6C--.

At col. 11, line 9, replace "FIG 5A-5D" with --FIGS. 5A-5B--.

At col. 11, line 10, replace "CDNA" with --cDNA--.

At col. 11, line 50, replace "32p" with --$^{32}$P--.

At col. 12, line 23, replace "CDNA" with --cDNA--.

At col. 13, line 46, replace "MRNA" with --mRNA--.

At col. 14, line 26, replace "08/402,888" with --08/472,888--.

At col. 14, line 29, replace "CH2" with --$CH_2$--.

UNITED STATES PATENT AND TRADEMARK OFFICE
CERTIFICATE OF CORRECTION

PATENT NO. : 5,858,752
DATED : Jan. 12, 1999
INVENTOR(S) : Brian Seed and Jan Holgersson It is certified that error appears in the above-identified patent and that said Letters Patent is hereby corrected as shown below:

At col. 14, line 42, replace "Fc" with --$F_c$--.

Signed and Sealed this

Thirtieth Day of November, 1999

Q. TODD DICKINSON

Attest:

Attesting Officer

Acting Commissioner of Patents and Trademarks